(12) United States Patent
Wang et al.

(10) Patent No.: US 9,380,991 B2
(45) Date of Patent: Jul. 5, 2016

(54) COMPUTERIZED TOMOGRAPHY (CT) METHOD AND CT SYSTEM

(71) Applicant: GE MEDICAL SYSTEMS GLOBAL TECHNOLOGY COMPANY, LLC, Waukesha, WI (US)

(72) Inventors: Xueli Wang, Beijing (CN); Zhenhua Xu, Beijing (CN); Yanling Qu, Beijing (CN); Ximiao Cao, Beijing (CN)

(73) Assignee: GE MEDICAL SYSTEMS GLOBAL TECHNOLOGY COMPANY, LLC, Waukesha, WI (US)

( * ) Notice: Subject to any disclaimer, the term of this patent is extended or adjusted under 35 U.S.C. 154(b) by 207 days.

(21) Appl. No.: 14/166,005

(22) Filed: Jan. 28, 2014

(65) Prior Publication Data

US 2014/0211912 A1 Jul. 31, 2014

(30) Foreign Application Priority Data

Jan. 31, 2013 (CN) .......................... 2013 1 0038053

(51) Int. Cl.
*A61B 6/00* (2006.01)
*A61B 6/03* (2006.01)
*G06T 11/00* (2006.01)

(52) U.S. Cl.
CPC ............... *A61B 6/5205* (2013.01); *A61B 6/032* (2013.01); *A61B 6/4078* (2013.01); *A61B 6/5258* (2013.01); *G06T 11/005* (2013.01); *G06T 2211/432* (2013.01)

(58) Field of Classification Search
USPC ......................................................... 378/1, 4
See application file for complete search history.

(56) References Cited

U.S. PATENT DOCUMENTS 7,254,259 B2 8/2007 Hsieh et al.
2011/0096968 A1* 4/2011 Deykoon ............... A61B 6/032
382/131

* cited by examiner

*Primary Examiner* — Nicole Ippolito
*Assistant Examiner* — Hanway Chang
(74) *Attorney, Agent, or Firm* — GE Global Patent Operation

(57) ABSTRACT

A computerized tomography (CT) method and CT system. The method comprises projecting a beam from a radiation source within a display field of view (DFOV) toward a subject to be imaged; receiving, at a detector, the projected beam to collect projection data; determining whether in the projection a truncation occurs in which the subject exceeds the DFOV; and recording a truncated location of the projection if truncation occurs.

16 Claims, 2 Drawing Sheets

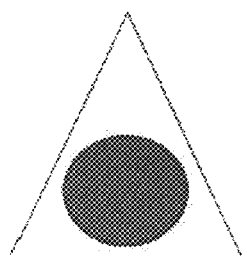
FIG. 1A Normal scenario
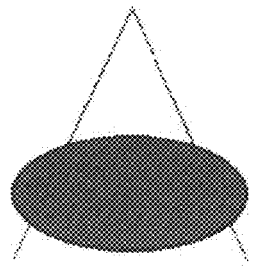
FIG. 1B Truncation scenario
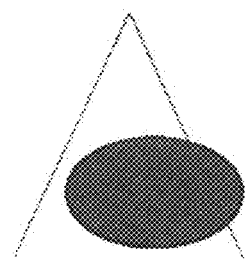
FIG. 1C Truncation scenario
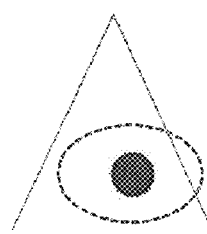
FIG. 1D Truncation scenario in off-center reconstruction
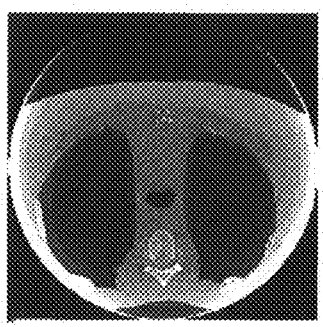
FIG. 2A
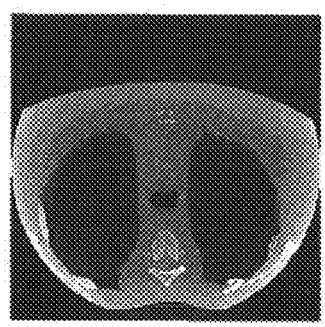
FIG. 2B
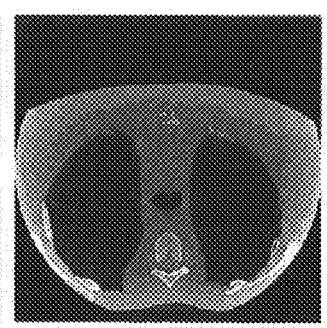
FIG. 2C

COMPUTERIZED TOMOGRAPHY (CT) METHOD AND CT SYSTEM

TECHNICAL FIELD

The present disclosure relates to a computerized tomography (CT) method and CT system.

BACKGROUND TECHNOLOGY

As is known in the art, CT is a method to make full use of acquired information and image to diagnose diseases, which maintains a certain field of view (FOV) through one examination. However, there is chance that the imaged subject exceeds the FOV, which is generally referred to in the art as a truncation. FIG. 1A illustrates a normal scan scenario and three truncation scenarios, which are respectively shown in FIG. 1B, FIG. 1C, and FIG. 1D.

If a truncation occurs, a bright external ring having roughly a width of twenty pixels sometimes appears in the reconstructed image, as shown in FIG. 2A. FIG. 2A shows an image from a radiograph for a chest, in which a bright external ring occurs due to applying zero padding to an original data of the truncated region in filtering for image construction. Although the bright ring gives hint of the truncated region, it loses real edge image information and thus degrades the image quality.

Typically, conventional CT systems extrapolate truncated projection data to reduce image discontinuity artifacts. Generally, two approaches are widely used in the art. One is to apply a nearest padding to the projection data of the truncated region in filtering for image construction, as shown in FIG. 2B. The other approach is mirror padding, which mirrors the previous projection data to the truncated region in filtering for image construction, as shown in FIG. 2C. However, it is hard to accurately predict the data trend of the truncated region in actual practice due to the complicated structure of a human body. Consequently, the image processed using either of these two approaches is not real with respect to the presentation of the truncated region. However, the presentation characteristics of the image, for example, the pixel brightness, are always used by a physician in actual practice to diagnose. Unfortunately, due to unreal presentation, the truncated region obtained with the aforesaid two approaches cannot be used for diagnosis purpose. Therefore, a physician needs to know which regions of the image are truncated so that the truncated regions will not be used to incur a misdiagnosis. Although the aforesaid two approaches increase the image quality around the truncated region, they lose the bright rings as well. In the absence of the bright rings, a physician will not be able to determine which regions are truncated when reviewing an image. Most of the physicians have doubts to the nearest padding scenario, the mirror padding scenario, and the off-center reconstruction, because they have no way to know which region or location of the image is destroyed by truncation. Besides, most of the conventional CT methods aim at correcting truncation. For example, U.S. Pat. No. 7,254,259, titled "Method and Apparatus for compensating truncation", which is incorporated herein by reference, merely teaches how to compensate truncation. In view of above, the physicians remain unable to know which regions are truncated while reviewing an image.

SUMMARY OF THE INVENTION

The object of the present disclosure is to address the aforesaid problems.

To address the aforesaid problems, the present disclosure proposes a computerized tomography (CT) method, comprising: projecting a beam from a radiation source within a display field of view (DFOV) toward a subject to be imaged; receiving, at a detector, the projected beam to collect projection data; determining whether in the projection a truncation occurs in which the subject exceeds the DFOV; and recording a truncated location of the projection if truncation occurs.

According to one embodiment, the method of the present disclosure further comprises: rotating the radiation source and the detector around the subject to emit a projection at a series of angles; determining whether the projection, at each of the angles, is truncated; and recording the truncated location if truncation occurs.

According to one embodiment, the method of the present disclosure further comprises: rotating the radiation source and the detector around the subject to emit a projection at a series of angles; determining whether the projection, at each angle within a certain range of angles, is truncated; and recording the truncated location if truncation occurs.

According to one embodiment, the method of the present disclosure further comprises: reconstructing an image based on the projection data; and marking the truncated location in the reconstructed image.

According to one embodiment, the reconstructed image is displayed on a user interface (UI), with the truncated location being marked by a visualization representation.

According to one embodiment, k is 0.97.

According to one embodiment, the truncated location is recorded as a tangent point for a boundary line of a fan-shaped projection range with a scan FOV.

According to one embodiment, the method of the present disclosure further comprises: if a truncation has occurred, determining whether the projection data for use in off-center reconstruction is influenced by the truncation; and if so, recording an influenced point for the off-center reconstruction.

According to one embodiment, the method of the present disclosure further comprises: rotating the radiation source and the detector to emit a projection at a series of angles; determining, at each angle, whether the projection data for use in off-center reconstruction is influenced by the truncation; and if so, recording the influenced point for the off-center reconstruction.

According to one embodiment, the method of the present disclosure further comprises: rotating the radiation source and the detector to emit a projection at a series of angles; determining, at each angle in a range of angles, whether the projection data for use in off-center reconstruction is influenced by the truncation; and if so, recording the influenced point for the off-center reconstruction.

According to one embodiment, said determining whether the projection data for use in off-center reconstruction is influenced by the truncation comprises: computing an influence range that is influenced by the truncation; computing a DFOV range for off-center reconstruction $DFOV_{off}$; and determining whether $DFOV_{off}$ and the computed influence range overlap.

According to one embodiment, the computed influence range is denoted by a number of corresponding detector channels.

According to one embodiment, if the truncation occurs at a lower end of the detector, the influence range is computed according to the following Equation:

$$[ch_{center} - N_{dfov}, ch_{center} - N_{dfov} + N_{kernel}/2].$$

The $ch_{center}$ denotes a detector central channel index; $N_{dfov}$ denotes a number of one half of the detector channels corresponding to the DFOV; $N_{kernel}$ denotes the size of a filter kernel denoted by a number of corresponding detector channels.

According to one embodiment, if the truncation occurs at a higher end of the detector, the influence range is computed according to the following Equation:

$$[ch_{center}+N_{dfov}-N_{kernel}/2, Ch_{center}+N_{dfov}].$$

The $ch_{center}$ denotes a detector central channel index; $N_{dfov}$ denotes a number of one half of the detector channels corresponding to the DFOV; $N_{kernel}$ denotes the size of a filter kernel denoted by a number of corresponding detector channels.

According to one embodiment, the Ndfov is computed according to the following Equation:

$$N_{dfov} = \frac{\text{Arcsin} \frac{maxDFOV/2}{D_{source-center}} * D_{source-detector}}{\text{Detector Module Size}}. \quad (1)$$

The $D_{source-detector}$ denotes a distance between the radiation source and the detector; $max_{DFOV}/2$ denotes a radius of a circle corresponding to the maximum DFOV; $D_{source-center}$ denotes a distance between the radiation source and an ISO center; and DetectorModuleSize denotes a size of a detector element that corresponds to a single channel.

According to one embodiment, a lower margin of the DFOV$_{off}$ is computed according to the following Equation:

$$lowerMargin = ch_{center} + \frac{\arctan \frac{C_{LRoff} - DFOV_{off}/2}{D_{source-center} - C_{APoff}} \times D_{source-detector}}{\text{Detector Module Size}},$$

and
a higher margin of the DFOV$_{off}$ is computed according to the following Equation:

$$higherMargin = ch_{center} + \frac{\arctan \frac{C_{LRoff}}{D_{source-center} - C_{APoff}} \times D_{source-detector}}{\text{Detector Module Size}} \times 2.$$

The $ch_{center}$ denotes a detector central channel index; DFOV$_{off}$/2 denotes a radius of a circle corresponding to the DFOV$_{off}$; $C_{LRoff}$ denotes a horizontal component of an offset of the center of the DFOV$_{off}$ circle relative to the ISO center; $C_{APoff}$ denotes a vertical component of the offset of the center of the DFOV$_{off}$ circle relative to the ISO center; $D_{source-detector}$ denotes a distance between the radiation source and the detector; $D_{source-center}$ denotes a distance between the radiation source and the ISO center; and DetectorModuleSize denotes a size of a detector element corresponding to one single channel.

According to one embodiment, the influence range is computed, in a helical scan mode, by considering data interpolation.

According to one embodiment, the computed DFOV$_{off}$ is denoted by a number of corresponding detector channels.

According to one embodiment, the influenced point is recorded as a tangent point for the offcenter reconstruction DFOV with a boundary line of a corresponding fan-shaped projection range.

According to one embodiment, the method of the present disclosure further comprises: performing an offcenter reconstruction; and providing a mark for the influenced point on the offcenter reconstructed image.

According to one embodiment, the off-center reconstructed image is displayed on a user interface, with the influenced point being marked by a visualization representation.

Disclosed in the present disclosure is also a computerized tomography (CT) system, which comprises: a radiation source for projecting a beam within a display field of view (DFOV) toward a subject to be imaged; a detector for receiving the projected beam to collect projection data; and a computer coupled to the radiation source and the detector and configured to determine whether in the projection a truncation occurs in which the subject exceeds the DFOV; and recording a truncated location of the projection if truncation occurs.

According to one embodiment, the radiation source and the detector are rotated around the subject to emit a projection at a series of angles. The computer is further configured to determine whether the projection, at each of the angles, is truncated, and to record the truncated location if truncation occurs.

According to one embodiment, the radiation source and the detector are rotated around the subject to emit a projection at a series of angles. The computer is further configured to determine whether the projection, at each angle within a certain range of angles, is truncated; and record the truncated location if truncation occurs.

According to one embodiment, the computer is further configured to reconstruct an image based on the projection data, and to mark the truncated location in the reconstructed image.

According to one embodiment, the CT system further comprises a user interface (UI) configured to display the reconstructed image, with the truncated location being marked by a visualization representation.

According to one embodiment, k is 0.97.

According to one embodiment, the computer is configured to recording the truncated location as a tangent point for a boundary line of a fan-shaped projection range with a scan FOV.

According to one embodiment, the computer is further configured to, if a truncation has occurred, determine whether the projection data for use in off-center reconstruction is influenced by the truncation, and to, if so, record an influenced point for the off-center reconstruction.

According to one embodiment, the radiation source and the detector are rotated around the subject to emit a projection at a series of angles, and the computer is further configured to determine, at each angle, whether the projection data for use in off-center reconstruction is influenced by the truncation; and to, if so, record the influenced point for the off-center reconstruction.

According to one embodiment, the radiation source and the detector are rotated around the subject to emit a projection at a series of angles, and the computer is further configured to determine, at each angle within a certain range of angles, the projection data for use in off-center reconstruction is influenced by the truncation; and if so, record the influenced point for the off-center reconstruction.

According to one embodiment, the computer is further configured to: compute an influence range that is influenced by the truncation; compute a DFOV range for off-center reconstruction DFOV$_{off}$; and determine whether DFOV$_{off}$ and the computed influence range overlap to determine whether the projection data for use in off-center reconstruction is influenced by the truncation.

According to one embodiment, the computed influence range is denoted by a number of corresponding detector channels.

According to one embodiment, if the truncation occurs at a lower end of the detector, the influence range is computed according to the following Equation:

$$[ch_{center} - N_{dfov}, ch_{center} - N_{dfoc} + N_{kernel}/2].$$

The $ch_{center}$ denotes a detector central channel index; $N_{dfov}$ denotes a number of one half of the detector channels corresponding to the DFOV; $N_{kernel}$ denotes the size of a filter kernel denoted by a number of corresponding detector channels.

According to one embodiment, The CT system according to any one of claims 36 and 37, wherein if the truncation occurs at a higher end of the detector, the influence range is computed according to the following Equation:

$$[ch_{center} + N_{dfov} - N_{kernel}/2, ch_{center} + N_{dfov}].$$

The $ch_{center}$ denotes a detector central channel index; $N_{dfov}$ denotes a number of one half of the detector channels corresponding to the maximum DFOV; $N_{kernel}$ denotes the size of a filter kernel denoted by a number of corresponding detector channels.

The CT system according to any one of claims 38 and 39, wherein Ndfov is computed according to the following Equation:

$$N_{dfov} = \frac{\text{Arcsin}\frac{maxDFOV/2}{D_{source-center}} * D_{source-detector}}{\text{Detector Module Size}}. \quad (1)$$

The $D_{source-detector}$ denotes a distance between the radiation source and the detector; maxDFOV/2 denotes a radius of the circle corresponding to the maximum DFOV; $D_{source-center}$ denotes a distance between the radiation source and an ISO center; and DetectorModuleSize denotes a size of a detector element that corresponds to a single channel.

According to one embodiment, the influence range is computed, in a helical scan mode, by considering data interpolation According to one embodiment, The CT system according to claim 36 or 42, wherein a lower margin of the DFOVoff is computed according to the following Equation:

$$lowerMargin = ch_{center} + \frac{\arctan\frac{C_{LRoff} - DFOV_{off}/2}{D_{source-center} - C_{APoff}} \times D_{source-detector}}{\text{Detector Module Size}},$$

and
a higher margin of the DFOVoff is computed according to the following Equation:

$$higherMargin = ch_{center} + \frac{\arctan\frac{C_{LRoff}}{D_{source-center} - C_{APoff}} \times D_{source-detector}}{\text{Detector Module Size}} \times 2.$$

The $ch_{center}$ denotes a detector central channel index; DFO-$V_{off}/2$ denotes a radius of the circle corresponding to the DFOV$_{off}$; $C_{LRoff}$ denotes a horizontal component of an offset of the center of the DFOV$_{off}$ circle relative to the ISO center; CAP$_{off}$ denotes a vertical component of the offset of the center of the DFOV$_{off}$ circle relative to the ISO center; D$_{source-detector}$ denotes a distance between the radiation source and the detector; D$_{source-center}$ denotes a distance between the radiation source and the ISO center; and DetectorModuleSize denotes a size of a detector element corresponding to a single channel.

According to one embodiment, the computed DFOV$_{off}$ is denoted by a number of corresponding detector channels.

According to one embodiment, the computer is further configured to record the influenced point as a tangent point for the off-center reconstruction DFOV with a boundary line of the corresponding fan-shaped projection range.

According to one embodiment, the computer is further configured to perform an off-center reconstruction, and providing a mark for the influenced point on the off-center reconstructed image.

According to one embodiment, the CT system further comprises a user interface (UI) for displaying the off-center reconstructed image, with the influenced point being marked by a visualization representation.

As compared with the conventional technology, the CT method proposed in the present disclosure detects occurrence of a truncation of a CT projection and records the truncated location, such that the user has knowledge of the truncated location and avoids applying the truncated region of an image for diagnosis, thereby increasing the accuracy in diagnosis.

In addition, the CT method of the present disclosure provides visualized clues of the truncated location on a user interface, facilitating the user to determine which region(s) are truncated and thus cannot be used for diagnosis. Therefore, the CT method is more satisfactory to the user.

Furthermore, while performing a CT projection to obtain projection data, the method of the present disclosure automatically detects the occurrence of truncation and records the truncated location, enabling a user to directly and conveniently obtain an indication of the truncated location.

What's more, due to the automatic recording of the truncated location while performing a CT projection, the CT method of the present disclosure provides an indication of the truncation more conveniently such that a user does not need to conduct additional manual computations or operations, making the whole workflow more personalized.

While providing the aforesaid benefits, the CT method of the present disclosure does not create any image artifacts.

Since the truncated location is recorded, a user may choose whether or not to display the truncated location on a user interface, providing a more satisfactory scheme.

More advantages and benefits of the present disclosure will be more apparent from the follow rig detailed descriptions.

BRIEF DESCRIPTION OF THE DRAWINGS

FIGS. 1A, 1B, 1C, and 1D illustrate a number of scenarios that may be encountered while scanning a subject clinically with a CT system. FIG. 1A shows a normal scenario in which the scanned subject is located centrally within the FOV; FIG. 1B shows a truncation scenario in which both sides of the scanned subject exceed the FOV; and FIG. 1C shows another truncation scenario in which one side of the scanned subject exceeds the FOV; and FIG. 1D shows an off-center reconstruction based on the scenario as shown in FIG. 1C.

FIGS. 2A, 2B, and 2C illustrate an image obtained by processing with the truncated region in a conventional CT system. FIG. 2A shows an image obtained by applying a zero padding to the truncated region; FIG. 2B shows an image obtained by applying a nearest padding to the truncated region; and FIG. 2C shows an image obtained by applying a mirror padding to the truncated region.

FIG. 4A illustrates the image obtained by applying a mirror padding, while FIG. 4B illustrates the image obtained with the method according to one embodiment of the present disclosure.

DETAILED DESCRIPTION OF THE DISCLOSURE

Figure 3:
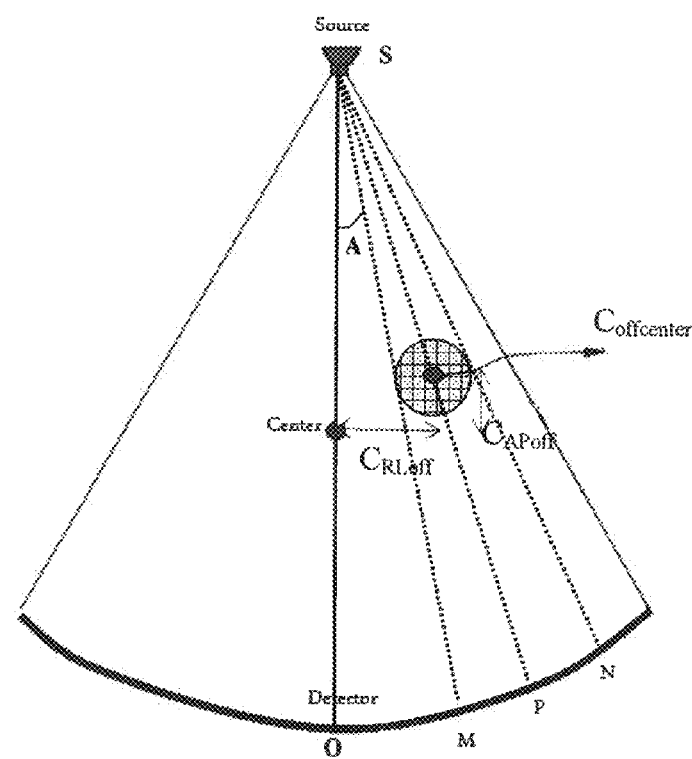
FIG. 3 is a schematic diagram of an off-center reconstruction with a method according to one embodiment of the present disclosure.

The embodiments employed in the present disclosure will be described hereunder in sufficient details by reference to the drawings such that persons skilled in the art would be able to carry out the present disclosure. It should be appreciated that other embodiments may be employed, and that modifications may be made to the logical, mechanical, and electrical aspects, etc. without deviating from the spirit of the present disclosure. Therefore, the following embodiments should not be read in a sense of limiting the scope of the present disclosure.

Truncation always occurs in the applications with the conventional CT systems. To avoid misdiagnosis or due to technical limitations, some CT systems do not calibrate the truncation by, for example, applying the nearest padding or mirror padding. Of course, this inevitably degrades the image quality, because the truncation destroys the near-by projection data. On the other hand, although some other CT systems conduct calibration with respect to the truncated region in filtering for image construction, it is still difficult to predict the data trend in filtering for image construction since the truncation could happen to any complicated human body region. The calibration may render the image unreal, so the truncated region, although calibrated, is still undesirable for diagnosis. The user, for example, a physician, will not be able to determine a truncated region from the calibrated image.

The CT method according to the present disclosure is capable of automatically detecting a truncated CT projection and recording the truncated location, enabling a user to easily obtain the truncated location and thereby identify in the reconstructed image a truncated region or a region that is influenced or destroyed by truncation.

The particular embodiments of the present disclosure will be described in details hereunder, and it should be appreciated that the present disclosure is not limited to these embodiments.

In a CT system, a radiation source and a detector are generally disposed on a rotary gantry that rotates around the scanned subject, for example, a patient, such that they rotate around the scanned subject within an imaging plane. The scanned subject is disposed on a table which moves or translates through the gantry. The radiation source projects a fan-shaped beam towards the subject, which beam is attenuated through the subject to be imaged. The attenuated beam then impinges upon an array of radiation detectors. Every detector element within the array produces a separate electrical signal that is a measure of the beam attenuation at the detector element. Each detector element corresponds to a channel, and the attenuation measures (i.e., the projection data) from all the detector elements are acquired separately to reconstruct a CT image.

In addition, the radiation source and the detector array may be rotated with a gantry within the imaging plane and around the subject to be imaged such that an angle (i.e. a view angle) at which the radiation beam intersects the subject constantly changes. At each view angle, a group of radiation attenuation measures, i.e., projection data, from the detector array corresponds to a "view". A "scan" of the subject includes a set of views or a set of projection data, obtained at a series of view angles, during one revolution of the radiation source and detector. Such a set of projection data may be used to construct a CT image of the scanned subject.

The method disclosed in the present disclosure is described hereunder in connection with different clinical scenarios.

In actual clinical applications, it is likely that a subject, large in size, may exceed the display field of view (DFOV), i.e., a truncation is likely to happen.

In general, two scan modes are clinically applied. One is a scan with a maximum DFOV and the other is off-center reconstruction with a smaller DFOV to observe a detailed part of the scanned subject. Hereunder the method according to the present disclosure is described in conjunction with the aforesaid scan modes in which a truncation may occur.

The method according to the present disclosure is described below in conjunction with the maximum DFOV scan mode, as shown in FIG. 1B and FIG. 1C.

Generally, during the operation of a CT system, in one view or at one view angle as shown in FIG. 1B and FIG. 1C, the vertex represents a radiation source, which emits a fan shaped beam within the maximum DFOV (or scan FOV) toward a subject to be imaged which is represented by a shadow. A detector (not shown) underneath receives the projected beam to obtain projection data.

Subsequently, Step I is executed for the projection at issue to determine whether the projection at issue is truncated or not.

Whether the projection is truncated or not may be determined based on the beam received by the detector in the margin of the DFOV. In particular, if the beam received in the margin of the DFOV is found to be attenuated by the subject, it is determined that a truncation happens to the projection. Otherwise, no truncation is found.

For example, a measure $V_{margin}$ is obtained for the beam received at the detector element channel in the margin of the DFOV, and then compared with a measure $V_{air}$ of the beam, which is received at the same detector channel without being attenuated by the subject (i.e., received after traversing air only). If $V_{margin}$ is smaller than $V_{air}$, it means that the beam in the margin of the DFOV is attenuated by a subject other than air, for example, the scanned subject. In other words, the scanned subject exceeds the margin of the DFOV, the projection is truncated. Otherwise, in the case of $V_{margin}$ being equal to $V_{air}$, it means that the projection is not truncated.

Obviously, $V_{air}$ disclosed herein is a constant, which may be stored in advance by a CT manufacturer in a CT system for future use when the CT system is manufactured.

$V_{margin}$ may be obtained in different ways than the above. Preferably, $V_{margin}$ may be an average of the measures at an edge channel N and at another channel. For example, $V_{margin}$ may be the average of the measure at the edge channel N and the measure at the adjacent channel N−1.

Disclosed hereinabove is an ideal scenario where no truncation is determined to have happened when $V_{margin}$ is equal to $V_{air}$. However, in actual practice, even though a truncation did not happen, $V_{margin}$ would not be equal to $V_{air}$ due to the manufacture and long-term use of the CT system. It may equal to $k*V_{air}$ (0<k<1, for example, 0.97). Of course, it should be appreciated that k is empirically determined by a manufacture according to experiences or experiments.

In view of above, the criterion for determining occurrence of a truncation may be expressed as follows:

$$TruncateLabel = \begin{cases} 1 & \text{if } V_{margin} < k * V_{air} \\ 0 & \text{else} \end{cases}$$

wherein Logic value "1" means occurrence of truncation, while logic "0" means no truncation.

If a truncation is determined to occur in Step I, Step II is then executed to record the truncated location of the truncated projection.

In particular, if Step I determines that a projection is truncated, the truncated point is recorded.

For example, as shown in FIG. 1C, the tangent point for the right boundary of the fan-shaped projection range with the scan FOV is the truncated point to be recorded. Although a circle corresponding to the scan FOV is not shown, the scan FOV is a familiar term in the art of CT image reconstruction and will not be introduced in details herein. Persons skilled in the art would appreciate that for a particular view angle, the tangent point is known or may be obtained upon known algorithms.

The truncated point may be stored in a computer as part of the projection data, and may be used in the future image reconstruction for presentation before the user.

According to one example, the radiation source and the detector rotate through a series of view angles. For each of these view angles, Steps I and II are executed for the respective projection when the radiation source and the detector are operated to obtain the respective projection data.

According to another example, the user, for example, a physician, may select a certain range of angles, for each view angle of which, Steps I and II are executed when the radiation source and the detector are operated to obtain the corresponding projection data.

Thereafter, the user may choose to execute Step III, if necessary, to reconstruct an image and mark the recorded truncated point in the reconstructed CT image.

Figures 4A, 4B:
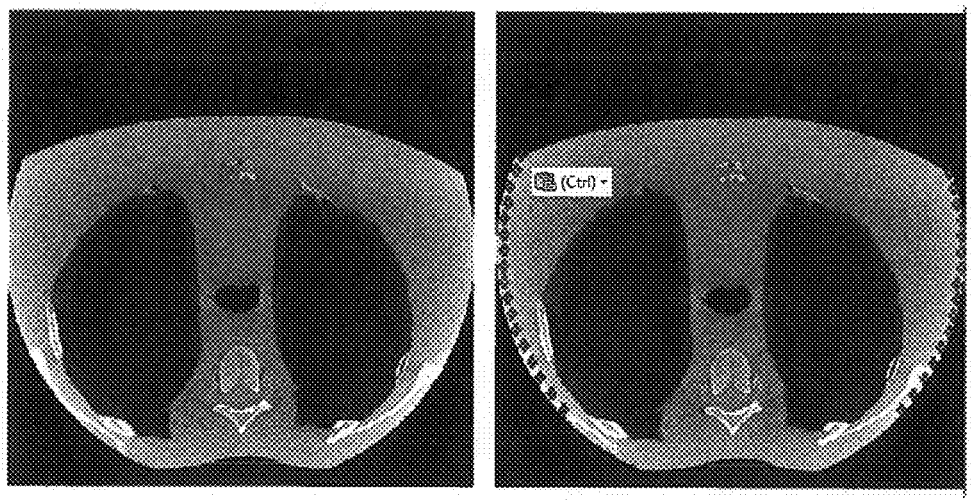
FIGS. 4A and 4B illustrate a comparison of an image obtained by applying mirror padding to the truncated region with an image obtained with a method according to one embodiment of the present disclosure.

In particular, after scanning the subject from a series of view angles, the marks for the truncated points are displayed in the reconstructed CT image on a user interface, as shown in FIG. 4B, so as to display the truncated region before the user.

It would be appreciated that in actual practice, the user may choose whether to display the truncated location in the reconstructed image according to preferences or circumstances.

The method disclosed in this embodiment may be used in combination with the conventional CT systems. For example, it may be combined with the conventional methods for correcting, compensating and calibrating truncation to enable a user to conveniently obtain a mark for the truncated location.

Now reference is made to FIG. 1D and FIG. 3 to describe a method of the present disclosure in connection with off-center reconstruction with a smaller DFOV.

In practical clinical applications, the user, for example, a physician always selects a more detailed part of a subject for reconstruction so as to establish the image thereof, as shown in FIG. 1D. Such a reconstruction is referred to as off-center reconstruction.

Steps I, II, and III described hereinabove in the previous embodiment are also applicable to this embodiment.

First, a determination is made to whether an off-center reconstruction is necessary. If so, the radiation source projects, at a certain view angle, a fan-shaped beam toward the subject, and then the projected beam is received by the detector.

Subsequently, Step I is performed for the projection at issue to determine whether the projection at issue is truncated. If so, Step S is then executed to determine whether the truncation influences the off-center reconstruction projection data. In other words, it is determined whether the detailed part is influenced or destroyed by the truncation. The particular steps are described as follows (Steps S1 through S3):

Step S1: influence range influenced by the truncation is calculated. The influence range means a region around truncation for which the projection data is destroyed in filtering for the image reconstruction due to truncation.

Generally, the parameters to be defined hereinafter and the influence range to be computed may be denoted by a number of corresponding detector channels.

The size of a filter kernel used for image reconstruction is defined as $N_{kernel}$ (identified by a number of corresponding detector channels); a central detector channel index is defined as $ch_{center}$; and one half of the detector channels corresponding to the DFOV is defined as $N_{dfov}$, then $$N_{dfov} = \frac{\text{Arcsin} \frac{maxDFOV/2}{D_{source-center}} * D_{source-detector}}{\text{Detector Module Size}} \quad (1)$$

wherein $D_{source-detector}$ denotes a distance between the radiation source and the detector; maxDFOV/2 denotes the radius of the circle corresponding to the maximum DFOV (i.e., the scan FOV); $D_{source-center}$ denotes a distance between the radiation source and an ISO center (i.e., the geometric center of the gantry); and DetectorModuleSize denotes the size of a single detector element. The aforesaid Equation (1) gives $N_{dfov}$.

If the truncation happens at a detector lower end, for example, the left side in FIG. 1B, the influence range may be computed according to the following Equation:

$$[ch_{center} - N_{dfov}, ch_{center} - N_{dfov} + N_{kernel}/2]$$

If the truncation happens at a detector higher end, for example, the right side as shown in FIG. 1B or the scenario as shown in FIG. 1C, then the influence range may be computed according to the following Equation:

$$[ch_{center} + N_{dfov} - N_{kernel}/2, ch_{center} + N_{dfov}]$$

Persons skilled in the art would appreciate that the "higher end" and the "lower end" referred to herein are used for ease of illustration only, and is not intended for limitation, Therefore, different manufactures may choose different definitions according to circumstances. For example, the right side in FIG. 1B may be expressed as a lower end, while the left as a higher end.

It could be understood that the aforesaid descriptions are suited for a general scan mode.

Of course, persons skilled in the art would understand that in the case of a helical scan mode, the influence range may be calculated by considering data interpolation. In particular, in the case of the helical scan mode, the projection data of a reconstructed plane may be acquired by interpolating data of two related sample view angles, for example, view angles with a difference of 360°, or by interpolating data of conjugated adjacent sample view angles with a difference of 180°. Therefore, it would be appreciated that the influence range may be obtained in a helical scan mode by interpolating corresponding parameters of related samples.

Step S2: The range of the off-center reconstruction DFOV, expressed as $DFOV_{off}$, is computed (identified by a number of corresponding detector channels).

Reference is now made to FIG. 3. The shadowed small circle represents the circle corresponding to $DFOV_{off}$. The offset at the center is defined as $C_{offcenter}$; the range for $DFOV_{off}$, a corresponding fan-shaped projection range, refers to the range between beam rays M and N as shown in FIG. 3. The underneath curve as shown in FIG. 3 represents the detector array.

To be more specific, the component of $C_{offcenter}$ along LR direction (the left and right directions in FIG. 3), and the component of $C_{offcenter}$ along AP direction (the up and down directions in FIG. 3) are respectively defined as $C_{LRoff}$ and $C_{APoff}$ to respectively represent the offset along LR direction for the center of the $DFOV_{off}$ circle, and the offset along AP direction for the same center. The offset in P direction is minus.

The detector center is defined as O; the radiation source as S, so the angle A between OS and SM is computed as follows:

$$A = \arctan \frac{C_{LRoff} - DFOV_{off}/2}{D_{source-center} - C_{APoff}}$$

wherein $DFOV_{off}/2$ denotes the radius of the $DFOV_{off}$ circle; $D_{source-detector}$ denotes a distance between the radiation source and the detector; and $D_{source-center}$ denotes a distance between the radiation source and the ISO center. The arc length of the curve OM is determined as $A*D_{source-detector}$.

Therefore, the lower margin of $DFOV_{off}$ (for example, M as shown in FIG. 3) is computed according to the following Equation (identified by a number of corresponding detector channels):

$$lowerMargin = ch_{center} + \frac{\arctan \frac{C_{LRoff} - DFOV_{off}/2}{D_{source-center} - C_{APoff}} \times D_{source-detector}}{\text{Detector Module Size}}$$

Likewise, the higher margin of $DFOV_{off}$ (for example, point N as shown in FIG. 3) is computed as follows (identified by a number of corresponding detector channels):

$$higherMargin = ch_{center} + \frac{\arctan \frac{C_{LRoff}}{D_{source-center} - C_{APoff}} \times D_{source-detector}}{\text{Detector Module Size}} \times 2$$

Step S3: a determination is made to whether $DFOV_{off}$ determined in Step S2 and the influence range determined in Step S1 overlap.

In particular, if they overlap, it means that the off-center reconstruction data is influenced by the truncation.

If Step I detects the occurrence of a truncation, Step II is then executed to record the truncated location of the projection, i.e., a first truncated point.

In addition to the first truncated point, if Step S3 determines the projection data for off-center reconstruction is influenced, the influenced point is recorded as a second truncated point. In particular, the second truncated point is recorded as the tangent point for the $DFOV_{off}$ with the boundary (corresponding to the line ON in FIG. 3) of the corresponding fan-shaped projection range.

According to one example, the radiation source and the detector rotate through a series of view angles. At each of these view angles, the aforesaid Steps I and II are executed, including Steps S1 through S3 when the radiation source and the detector may be operated to obtain corresponding projection data.

According to another example, the user, for example, a physician, may select a certain range of angles, for each view angle of which, Steps I and II are executed, including Steps S1 through S3.

Subsequently, Step III may be executed, if necessary, to reconstruct the image and mark the first truncated point on the reconstructed CT image. Particularly, after scanning the subject through a series of view angles or a certain range of view angles, the CT image is reconstructed for the scanned subject and the truncated location is marked in the image.

Step IV may then be executed, if necessary, to perform an off-center reconstruction, and in the off-center reconstructed CT image of the detailed part, a mark for the second truncated point is provided.

In one example, a physician may only need the image of a more detailed part. In this case, the physician may skip Step III to perform Step IV directly.

The method of this embodiment may be applied in conjunction with the conventional CT systems to automatically detect the truncation in the off-center reconstructed image of the detailed part and record the truncated location. It could be appreciated that the method disclosed herein may be used in combination with the conventional methods for correcting, compensating and calibrating truncation in order to provide a mark for any truncation to the user.

Embodiment 3

A CT system is disclosed in this embodiment, which comprises a radiation source for projecting a beam within DFOV toward a subject to be imaged; a detector for receiving the projected beam to collect projection data; and a computer coupled to the radiation source and the detector, the computer configured to perform the method of any of the foregoing embodiments.

According to one embodiment, the radiation source and the detector may be disposed on a gantry that rotates around a subject, for example, a patient. The CT system may further comprise a control mechanism for controlling the radiation source and the detector to rotate through a series of view angles while the CT is operating. For example, the control mechanism may supply, to the radiation source, power and timing signals, and supply, to a motor controller of the gantry, rotary speed and location signals to control the rotary speeds and locations of the radiation source and the detector disposed on the gantry.

The computer disclosed herein is not limited to an integrated circuit, but refers broadly to various computers, processors, micro-controllers, micro-computers, programmable logic controllers, specific integrated circuits or other programmable electric circuits.

In one example, the computer may be integrated, as an integrated circuit, into at least one of a data collecting system and an image reconstructer of the CT system to perform the method of any of the aforesaid embodiments.

Of course, although the embodiments of the present disclosure only mention a single computer configured to perform any methods disclosed hereinabove, the present disclosure is not limited hereby.

In one example, the computer may be divided into a plurality of modules to perform the methods disclosed hereinabove. These modules may be integrated into different units of the CT system according to circumstances, for example, a data collecting system, an image reconstructer and a user interface.

According to one example, the CT system further comprises a user interface configured to display the off-center reconstructed image. The influenced points may be marked by a visualization representation, for example, an icon and highlighting, on the user interface.

In one example, the CT system may further comprise a mass storage to store the reconstructed image and information related to the truncated location as an input.

According to one example, the user may view, from the user interface, the reconstructed image and choose to display the truncated location on the reconstructed image.

Of course, it would be appreciated that the methods disclosed in the present disclosure may be applied to a non-medical imaging system in, for example, industries and transportations, for example, a CT system for scanning luggage.

It bears mentioning that the aforesaid embodiments of the present disclosure are illustrative only, and should not be construed to limit the scope of the present disclosure. Persons skilled in the art would be able to design a number of alternative embodiments without deviating the scope of the present disclosure which should be defined by the appended claims. The term such as "include" used herein does not exclude elements and/or steps other than those in the claims or description. The word "a" or "an" preceding a element and/or step does not exclude the possibility of a plurality of these elements and/or steps concerned. Any parenthesized numerals or signs used in the claims for reference should not be construed to limit the scope of the claims'.

The present disclosure is not by any means limited to the foregoing embodiments. Persons skilled in the art would see it possible and obvious to modify the foregoing embodiment without deviating the scope of the disclosure that should be defined by the appended claims.

What is claimed is:

1. A computerized tomography (CT) method, comprising:
   projecting a beam from a radiation source within a display field of view (DFOV) toward a subject to be imaged;
   receiving, at a detector, the projected beam to collect projection data;
   determining whether a truncation in the projection occurs in which the subject exceeds the DFOV, comprising:
      obtaining a beam measure $V_{margin}$ at a channel corresponding to a margin of the DFOV;
      comparing $V_{margin}$ with $k*V_{air}$, wherein $V_{air}$ is a measure of a beam not being attenuated by the subject, wherein k is defined as $0<k<=1$; and
      if $V_{margin}$ is smaller than $k*V_{air}$, indicating an occurrence of a truncation; and
   recording a location of the indicated truncation of the projection.

2. The method according to claim 1, further comprising:
   rotating the radiation source and the detector around the subject to emit a projection at a series of angles;
   determining, at each of the series of angles, whether the projection is truncated; and
   recording as the location of the truncation, an angle of the truncation in the projection.

3. The method according to claim 1, further comprising:
   rotating the radiation source and the detector around the subject to emit a projection at a series of angles;
   determining, at each angle within a certain range of angles, whether the projection is truncated; and
   recording as the location of the truncation, an angle of the truncation in the projection.

4. The method according to claim 1, further comprising:
   reconstructing an image based on the projection data; and
   marking the truncated location in the reconstructed image.

5. The method according to claim 1, wherein the truncated location is recorded as a tangent point for a boundary line of a fan-shaped projection range with a scan field of view.

6. The method according to claim 1, further comprising:
   if a truncation is indicated, determining whether a projection data for use in off-center reconstruction is influenced by the truncation; and
   if the projection data for use in off-center reconstruction is influenced by the truncation, recording an influenced point for the off-center reconstruction.

7. The method according to claim 1, further comprising:
   rotating the radiation source and the detector to emit a projection at a series of angles;
   determining, at each angle, whether the projection data for use in off-center reconstruction is influenced by the truncation; and
   if the projection data for use in off-center reconstruction is influenced by the truncation, recording the influenced point for the off-center reconstruction.

8. A computerized tomography (CT) system, comprising:
   a radiation source for projecting a beam within a display field of view (DFOV) toward a subject to be imaged;
   a detector configured to receive the projected beam to collect projection data; and
   a processor, coupled to the radiation source and the detector and, configured to:
      obtain a beam measure $V_{margin}$ at a channel corresponding to a margin of the DFOV;
      compare $V_{margin}$ with $k*V_{air}$, wherein $V_{air}$ is a measure for the beam not being attenuated by the subject, wherein k is defined as $0<k<=1$; and
      if $V_{margin}$ is smaller than $k*V_{air}$, indicate an occurrence of a truncation in the projection; and
      record a location of the indicated truncation in the projection.

9. The CT system according to claim 8, wherein the radiation source and the detector are rotated around the subject to emit a projection at a series of angles, wherein the processor is further configured to:
   determine whether the projection, at each of the angles, is truncated, and
   record the truncated location if truncation occurs.

10. The CT system according to claim 8, wherein the radiation source and the detector are rotated around the subject to emit a projection at a series of angles, wherein the processor is further configured to:
    determine whether the projection, at each angle within a certain range of angles, is truncated, and
    record the truncated location if truncation occurs.

11. The CT system according to claim 8, wherein the processor is further configured to:
    reconstruct an image based on the projection data, and
    mark the truncated location in the reconstructed image.

12. The CT system according to claim 8, wherein the processor is further configured to record the truncated location as a tangent point for a boundary line of a fan-shaped projection range with a scan field of view.

13. The CT system according to claim 8, wherein the processor is further configured to:
    if a truncation is indicated, determine whether a projection data for use in off-center reconstruction is influenced by the truncation, and to, if the projection data for use in off-center reconstruction is influenced by the truncation, record an influenced point of the off-center reconstruction.

14. The C-T system according to claim 13, wherein the radiation source and the detector are rotated around the subject to emit a projection at a series of angles, and processor is further configured to determine, at each angle, whether the projection data for use in off-center reconstruction is influenced by the truncation, and, if the projection data for use in off-center reconstruction is influenced by the truncation, to record the influenced point of the off-center reconstruction.

15. The CT system according to claim 13, wherein the radiation source and the detector are rotated around the subject to emit a projection at a series of angles, and the processor is further configured to determine, at each angle within a certain range of angles, whether the projection data for use in off-center reconstruction is influenced by the truncation, and, if the projection data for use in off-center reconstruction is influenced by the truncation, to record the influenced point of the off-center reconstruction.

16. The CT system according to claim 13, wherein the processor is further configured to:
   compute an influence range influenced by the truncation;
   compute a DFOV range for off-center reconstruction (DFOVoff); and
   determine whether the DFOVoff and the computed influence range overlap to determine whether the projection data for use in off-center reconstruction is influenced by the truncation.

* * * * *